United States Patent [19]

Graub

[11] Patent Number: 5,211,561
[45] Date of Patent: May 18, 1993

[54] COUPLING DEVICE FOR DENTAL PROTHESIS

[75] Inventor: M. Walter Graub, Twann, Switzerland

[73] Assignee: Metaux Precieux sa Metalor, Neuchatel, Switzerland

[21] Appl. No.: 887,399

[22] Filed: May 21, 1992

[30] Foreign Application Priority Data

May 28, 1991 [CH] Switzerland .......................... 1579/91

[51] Int. Cl.[5] .............................................. A61C 13/28
[52] U.S. Cl. .................................... 433/169; 433/172; 433/181
[58] Field of Search ................ 433/169, 172, 181, 182

[56] References Cited

U.S. PATENT DOCUMENTS

| | | | |
|---|---|---|---|
| 1,665,154 | 3/1928 | Withycombe | 433/169 |
| 4,362,509 | 12/1982 | Sulc | 433/169 |
| 4,547,156 | 10/1985 | Hader | 433/172 |
| 5,098,295 | 5/1992 | Durr et al. | 433/169 |

FOREIGN PATENT DOCUMENTS

| | | |
|---|---|---|
| 0298909 | 1/1989 | European Pat. Off. . |
| 1104365 | 1/1960 | France . |
| 597843 | 4/1978 | Switzerland . |
| 646046 | 11/1984 | Switzerland . |
| 646047 | 11/1984 | Switzerland . |
| 650662 | 8/1985 | Switzerland . |
| 651194 | 9/1985 | Switzerland . |
| 651462 | 9/1985 | Switzerland . |
| 674926 | 8/1990 | Switzerland . |
| WO87/06816 | 11/1987 | World Int. Prop. O. . |

Primary Examiner—John J. Wilson

[57] ABSTRACT

A coupling for removable dental protheses comprising a male member one end of which is constituted by a fixing member, whereas the other end has the shape of a male coupling member and a female portion comprising a rigid casing fixed into the prothesis which houses a resiliently deformable mass provided with a housing intended to receive the male coupling member of the male portion. This resiliently deformable mass is maintained in the casing by a removable ring clipped on the casing so that the replacement of this mass is effected without any intervention on the prothesis. In one embodiment, the male coupling member is a cylinder connecting through a rib to a support and the female portion of the coupling comprises a cylindrical sleeve of resiliently deformable material maintained within the casing of the female portion of the coupling by a slotted ring, the ring comprising locking formations cooperating with corresponding formations of the casing and of the sleeve and fixing its angular service position with respect to these two parts. In another embodiment, the male coupling member is a sphere and the rigid casing is non-spherical, the resiliently deformable mass having a spherical cavity that receives and retains the sphere. The removable ring contacts and retains the resiliently deformable mass but is spaced from the male member.

3 Claims, 2 Drawing Sheets

COUPLING DEVICE FOR DENTAL PROTHESIS

BACKGROUND OF THE INVENTION

There are numerous existing systems for removable dental protheses making generally use of couplings of the press-button type one part of which, usually the male part, is fastened onto the jaw of the patient either in the bone or in a valid tooth, and the other part of which, the female part, is fastened in the prothesis. Such coupling devices are for example described in the following patents CH 646.046; CH 646.047; CH 651.462 and CH 651.194.

Most of these devices have the drawback of a too rigid fixing of the prothesis in the mouth, so that under the effect of shocks and efforts due to chewing of the food stuff, it is frequent that after a certain duration the cementing of the male part implanted into a valid tooth or into the jaw bone is loosened or destroyed.

In the device described in the patent CH 597.843 a fixing rider which is elastically deformable is put between the male and female part of the coupling giving a certain smoothness to the fixing of the prothesis. However, during the setting in place and the withdrawal of this prothesis, the resilient deformation of this rider transmits substantial forces to the prothesis. These forces make it necessary to provide important and very solid walls of the prothesis to avoid its deterioration and this increases the weight and the encumbrance of the prothesis in the mouth.

There are further other types of coupling permitting a removable fixing of a prothesis with a certain degree of smoothness which use male or female coupling members made in two parts which are resiliently deformable the one with respect to the other. The drawback of these devices is that the voids and spaces comprised between these two parts fill with detritus or tartar causing a bad hygiene of the mouth and a bad working of the coupling device.

Patent CH 674.926 discloses a coupling for removable dental prothesis which comprises a retention member which is fixed in the mouth, one end of which is formed by a threaded rod whereas the other has the shape of a portion of a sphere and a matrix comprising a rigid casing housing a resiliently deformable mass provided with a void intended to receive this spherical portion of the retention member. This matrix presents means for a rigid and definitive fixation into a prothesis.

The drawback of this type of coupling resides mainly in the fact that the resiliently deformable mass is rapidly weared off and that its characteristics are modified with the aging within the mouth.

SUMMARY OF THE INVENTION

The present invention has for its object a coupling for removable dental prothese of the type of the one described in the patent CH 674.926, but which, eliminates its major drawback. The coupling for removable dental prothesis distinguishes itself by the fact that the resiliently deformable mass is maintained in the casing through a removable ring clipped or snapped onto the said casing so that the replacement of this mass is effected without any intervention on the prothesis in which the housing is fixed.

BRIEF DESCRIPTION OF THE DRAWINGS

The attached drawings show schematically and by way of example two embodiments of the coupling device for a removable dental prothesis.

DETAILED DESCRIPTION OF THE PREFERRED EMBODIMENTS

Figure 1:
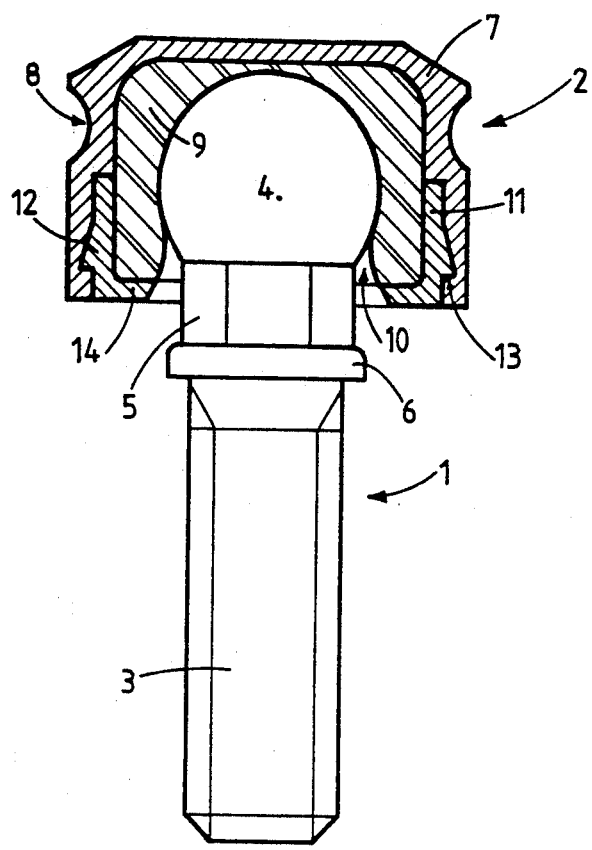
FIG. 1 shows in elevation a male portion of the coupling and in cross-section the female portion of said coupling, in coupled position, of a first embodiment of the coupling.
Figure 2:
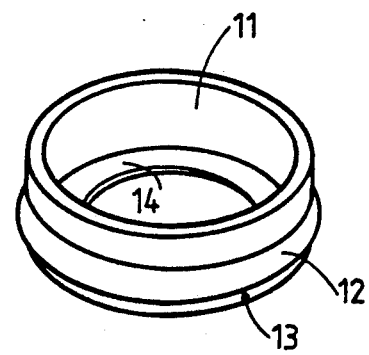
FIG. 2 shows in perspective view a retention ring of the female portion of the coupling shown in FIG. 1.

The first embodiment of the coupling device for removable dental protheses shown in FIGS. 1 and 2 comprises a male portion 1 and a female portion 2.

The male portion 1 of the coupling has a threaded rod 3 at one of its ends and at its other end a spherical part 4 connected to the threaded rod 3 through a polygonal zone 5 and a collar 6. The polygonal zone 5 is used as a nut to screw the threaded rod 3 into a tooth, a root or the bone of the jaw of the patient.

The female portion 2 of the coupling has a casing 7 comprising retaining formations 8, here a circular groove, permitting the incorporation of the casing into the molded mass of the dental prothesis, not shown. This casing houses a mass made of synthetic deformable material 9 presenting a spherical housing opening on the open face of the casing 7 through an aperture 10 comprising a narrowing, of a diameter less than that of the spherical housing. This spherical housing presents a diameter corresponding to that of the spherical terminal portion 4 of the male portion 1.

When the coupling is in service position FIG. 1, the spherical part 4 is firmly maintained within the housing of the deformable mass 9.

This deformable mass 9 is maintained in service position within the casing 7 by means of a maintaining ring 11 made of synthetic material comprising a circular extension 12 engaged in service position under the shoulder 13 of the outside wall of the casing 7. This ring comprises an annular portion 14 firmly maintaining the deformable mass 9 within the casing in service position.

The male and female portions 1, 3 of this coupling may be coupled and uncoupled easily by introducing or pulling this spherical part 4 into or out of the corresponding housing of the deformable mass 9, generally made out of synthetic material, through resilient deformation of this mass. The elasticity and/or the hardness of this resiliently deformable mass 9 are calculated and adjusted in order to obtain the desired retention force.

A protecting ring, not shown, can rest on the collar 6 and the outside face of the annular portion 14 of this ring 11 avoiding any obstruction of the opening 10 by food stuff.

The interest of this solution resides in the fact that when the mass made of resiliently deformable synthetic material, which is the only part of the coupling which is able to wear off or to age, is worn out or deformed by the normal working of the coupling it suffices to take the ring 11 and this mass 9 out of the casing 7 and to introduce in said casing a new mass 9 generally maintained by a new ring 11 so that the coupling be renewed at less cost without any intervention on the prothesis itself.

The second embodiment (FIGS. 3 and 4) of the coupling comprises a male portion 1, comprising a support 15 intended to be cemented into a tooth of the patient from which emerges a coupling member constituted by a cylinder 16 connected to the support 15 through a rib 17.

The female portion 2 of this coupling comprises a casing 18 intended to be fixed rigidly, or incorporated into a removable dental prothesis having a generally cylindrical shape presenting a central void and a lateral slot 19. A cylindrical sleeve 20 of synthetic deformable material is disposed in the void of the casing and is maintained in service position through a retention ring 21. This retention ring is slotted, its slot corresponds to the one 19 of the casing 18, and comprises a clipping formation 22 cooperating with a corresponding formation of the casing 18.

The internal diameter of the sleeve 20 is less than or equal to the outside diameter of the cylindrical part 16. The female portion 2 can thus be introduced over the male portion 1, the rib 17 passing into the slot 19 and the cylinder 16 is being housed in the sleeve 20.

In this embodiment, the retention force between the two parts of the coupling is obtained by the friction force between the sleeve 20 and the cylinder 16.

Here also the sleeve 20 is easily interchangable, increasing without limit the lifetime of such a coupling.

Figure 3:
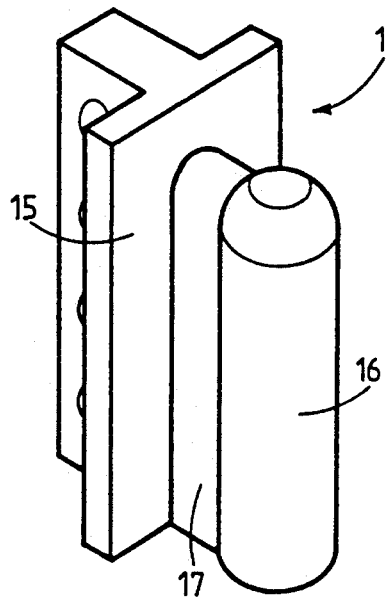
FIG. 3 shows in perspective view the male portion of a second embodiment of the coupling.
Figure 4:
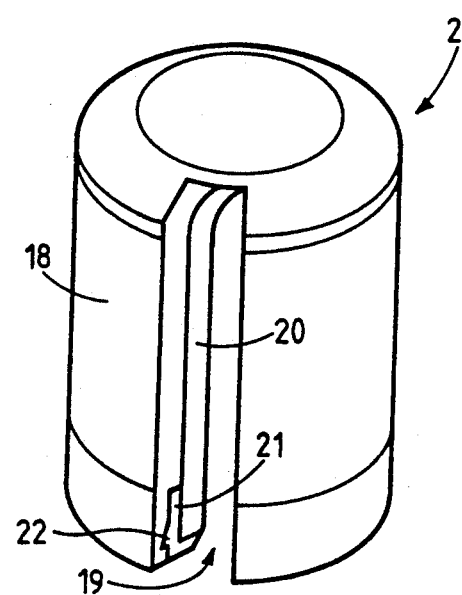
FIG. 4 shows in perspective view the female part of the second embodiment of the coupling.
Figure 5:
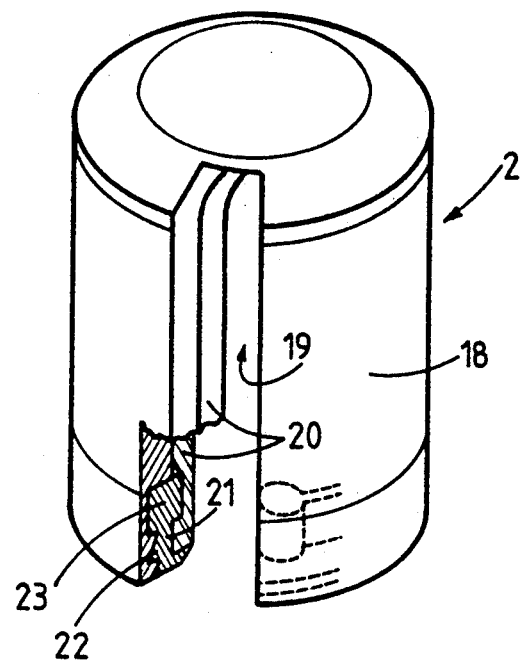
FIG. 5 shows in perspective view a third embodiment of the female part of the coupling.
Figure 6:
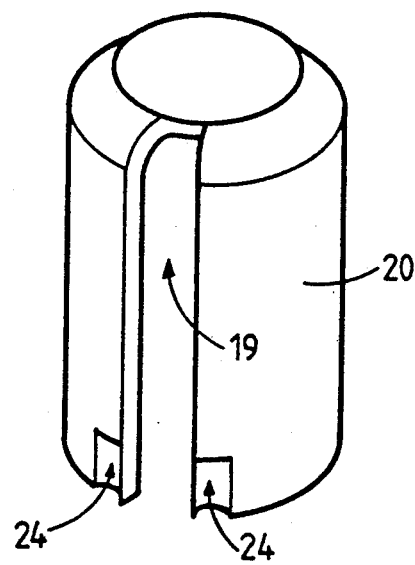
FIGS. 6 and 7 show constitutive parts of the female portion shown in FIG. 5.
Figure 7:
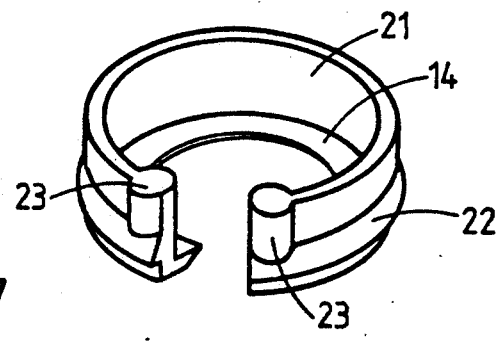

FIGS. 5 to 7 show a variant of the female part 2 of the coupling shown in FIGS. 3 and 4 and its constitutive parts, the sleeve 20 and the removable retention ring 21.

In this embodiment, the retention ring 21 comprises further locking formations 23 cooperating in service position simultaneously with corresponding formations 24 of the sleeve 20 and of the casing 18. Thus, the angular service position of the sleeve 20 and of the ring 21 is fixed.

The evident and enormous advantage of this coupling for a removable dental prothesis is to enable an unlimited use of the prothesis without harming this delicate piece. The simple exchange or replacement of the resiliently deformable mass 9, 20 enables renewing a worn out coupling.

I claim:

1. In a coupling for removable dental protheses comprising a male member one end of which is constituted by a fixing member, whereas the other end has the shape of a male coupling member and a female portion comprising a rigid casing fixed into the prothesis which houses a resiliently deformable mass provided with a housing intended to receive the male coupling member of the male portion; the improvement wherein this resiliently deformable mass is maintained in the casing by a removable ring clipped on the casing so that the replacement of this mass is effected without any intervention on the prothesis in which the said casing is fixed, the male coupling member being a cylinder connecting through a rib to a support and the female portion of the coupling comprises a cylindrical sleeve of resiliently deformable material maintained within the casing of the female portion of the coupling by means of a slotted ring, the ring comprising locking formations cooperating with corresponding formations of the casing and of the sleeve and fixing its angular service position with respect to these two parts.

2. Coupling according to claim 1, wherein the retention force of the coupling is determined by the friction forces existing between the sleeve and the cylinder.

3. In a coupling for removable dental protheses comprising a male member one end of which is constituted by a fixing member, whereas the other end has the shape of a male coupling member and a female portion comprising a rigid casing fixed into the prothesis which houses a resiliently deformable mass provided with a housing intended to receive the male coupling member of the male portion; the improvement wherein the male coupling member is a sphere and said rigid casing is non-spherical, said resiliently deformable mass having a spherical cavity that receives and retains said sphere, and a removable ring clipped on the casing and contacting and retaining the resiliently deformable mass but spaced from said male member.

* * * * *